US006455712B1

(12) United States Patent
Vaporciyan et al.

(10) Patent No.: US 6,455,712 B1
(45) Date of Patent: Sep. 24, 2002

(54) PREPARATION OF OXIRANE COMPOUNDS

(75) Inventors: Garo Garbis Vaporciyan, Amsterdam (NL); Brendan Dermot Murray, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/736,522

(22) Filed: Dec. 13, 2000

(51) Int. Cl.$^7$ .............................................. C07D 301/19
(52) U.S. Cl. ...................................................... 549/529
(58) Field of Search ......................................... 549/529

(56) References Cited

U.S. PATENT DOCUMENTS

| 3,350,422 | A |   | 10/1967 | Kollar |         |
|-----------|---|---|---------|--------|---------|
| 5,475,159 | A |   | 12/1995 | Singleton et al. | |
| 5,723,637 | A | * | 3/1998  | Tsuji et al. ................. | 549/529 |
| 6,011,162 | A | * | 1/2000  | Han et al. .................... | 549/529 |
| 6,160,137 | A | * | 12/2000 | Tsuji et al. ................. | 549/523 |

FOREIGN PATENT DOCUMENTS

| CS | 140743     |    | 3/1971  |
|----|------------|----|---------|
| WO | 94/22055   |    | 9/1994  |
| WO | 01/05778   | A1 | 10/2000 |
| WO | 01/70710   | A1 | 3/2001  |
| WO | 01/70711   | A1 | 3/2001  |
| WO | 01/70712   | A1 | 3/2001  |
| WO | 01/70713   | A1 | 3/2001  |
| WO | 01/70714   | A1 | 3/2001  |
| WO | 01/70715   | A1 | 3/2001  |

* cited by examiner

*Primary Examiner*—Alan L. Rotman
*Assistant Examiner*—Rita Desai
(74) *Attorney, Agent, or Firm*—Y. Grace Tsang

(57) ABSTRACT

A process for preparing oxirane compounds, which process comprises:

(i) oxidizing an alkylaryl to obtain a stream comprising alkylaryl hydroperoxide, (ii) contacting at least a part of the alkylaryl hydroperoxide obtained in step (i) with an olefin in the presence of a catalyst to obtain a product stream comprising an oxirane compound and alkylaryl hydroxyl, (iii) optionally reacting part of the alkylaryl hydroperoxide obtained in step (i) to obtain a mixture comprising (a) phenol, and (b) a ketone and/or aldehyde, and (c) optionally by-products, (iv) separating oxirane compound from the product stream of step (ii) to obtain (a) a residual product stream and (b) oxirane, and (v) contacting at least a part of the residual product stream with hydrogen to obtain alkylaryl, wherein at least a part of said alkylaryl is recycled to step (i).

16 Claims, No Drawings

PREPARATION OF OXIRANE COMPOUNDS

BACKGROUND OF THE INVENTION

The present invention relates to a process for the preparation of oxirane compounds.

Processes for preparing oxirane compounds such as propylene oxide are well known. NL-C-1010372 describes a process comprising reacting propene with ethylbenzene hydroperoxide to obtain propylene oxide and 1-phenyl ethanol. The 1-phenyl ethanol is subsequently dehydrated to obtain styrene, which is a useful starting material for other chemical reactions. NL-C-1012749 describes a similar process in which propene is reacted with cumenehydroperoxide to obtain propene oxide and 2-phenyl-2-propanol. The latter is described to be subsequently dehydrated into alpha-methylstyrene which is described to be an industrially applicable compound.

Suitable outlets can often be found for many of the products co-produced in the prior art processes for manufacturing oxirane compounds such as propylene oxide. However, it can be beneficial to be able to produce solely the oxirane compounds such as propylene oxide.

In EP-B-609455, a process is described for producing cresol by (1) oxidation of cymene to obtain a solution of oxygenation products containing tertiary hydroperoxide and primary hydroperoxide, (2) reduction of the content of primary hydroperoxide, (3) decomposition of the reaction mixture to obtain cresol and some by-products, and (4) subjecting the decomposition mixture to hydrogenation to convert part of the by-products to cymene and/or cresol. EPB-609455 solely relates to the preparation of cresol.

A process has now been found which makes it possible to prepare oxirane compounds without the need to prepare further compounds at the same time. Although some of the process steps of the process according to the present invention are known per se, there is no teaching or hint in the prior art to combine these process steps in this particular way.

SUMMARY OF THE INVENTION

The present invention relates to a process for the preparation of oxirane compounds, which process comprises:
(i) oxidizing an alkylaryl to obtain a stream comprising alkylaryl hydroperoxide,
(ii) contacting at least a part of the alkylaryl hydroperoxide obtained in step (i) with an olefin in the presence of a catalyst to obtain a product stream comprising an oxirane compound and alkylaryl hydroxyl,
(iii) optionally reacting part of the alkylaryl hydroperoxide obtained in step (i) to obtain a mixture comprising (a) phenol, and (b) a ketone and/or aldehyde, and optionally (c) by-products,
(iv) separating oxirane compound from the product stream of step (ii) to obtain (a) a residual product stream and (b) oxirane,
(v) contacting at least a part of the residual product stream with hydrogen to obtain alkylaryl,
wherein at least a part of said alkylaryl is recycled to step (i).

DETAILED DESCRIPTION OF THE INVENTION

Although ethylbenzene is the alkylaryl compound most widely used in the preparation of an oxirane compound at present, it has been found that process step (i) can be carried out at higher conversion and higher selectivity if the alkylaryl compound employed is an alkylbenzene in which the alkyl substituent is a branched alkyl substituent comprising from 3 to 10 carbon atoms. A more preferred alkylaryl compound contains 1 or 2 alkyl substituents. An alkylaryl compound containing several substituents has the advantage that it can contain several hydroperoxide groups. However, in view of potential side-reactions, it is preferred that there are no more than 3 substituents, more preferably no more than 2 substituents. Most preferably, the alkylaryl compound is cumene and/or di(iso-propyl)benzene. Although mixtures of different alkylaryl compounds can be employed, a single type of compound is preferred in order to be able to optimise the process conditions for this specific compound.

The oxidation of the alkylaryl can be carried out by any suitable process known in the art. The oxidation can be carried out in the liquid phase in the presence of a diluent. This diluent is preferably a compound which is liquid under the reaction conditions and does not react with the starting materials and product obtained. However, the diluent can also be a compound necessarily present during the reaction. For example, if the alkylaryl is cumene the diluent can be cumene as well.

The product obtained in step (i) can be used as such in step (ii), or it can be preferred to separate off some compounds, or it can be preferred to only use part of the product obtained and to use another part in another process.

Preferably, part of the product of step (i) is used in step (iii), namely reaction of the alkylaryl hydroperoxide to obtain phenol and ketone and/or aldehyde. The phenol obtained can contain substituents. The reaction of the alkylaryl hydroperoxide can be attained by contacting the alkylaryl hydroperoxide with a catalyst such as an acidic catalyst. As non-limiting illustrative examples of the acidic catalysts which can be used include, but not limited to, sulphuric acid, hydrochloric acid, perchloric acid, sulphur dioxide and sulphur trioxide; organic acids such as benzenesulphonic acid, p-toluenesulphboic acid, cresolsulphonic acid and chloroacetic acid; solid acids such as silica-alumina, alumina and acidic ion exchange resins; heteropolyacids such as tungstosilicic acid, tungstophosphoric acid and molybdophosphoric acid. Preferably, sulphuric acid and/or cresolsulphonic acid are used. The amount of catalyst to be used is usually in the range of from about 0.0001 to 1% wt, based on the reaction mixture to be treated. The reaction temperature is usually in the range of from 30 to 150° C.

The alkylaryl hydroperoxide can be subject to the reaction after other compounds have been separated off from the reaction product of step (i). However, it is preferred to subject part of the reaction product of step (i) directly to the reaction of step (iii).

The reaction in step (iii) usually produces by-products. In order to further increase the conversion into the desired products phenol and ketone and/or aldehyde, the desired products can be separated from the reaction product of step (iii) and at least part of the by-products obtained in step (iii) are sent to step (v). Product to be hydrogenated can be separated off and subsequently subjected to hydrogenation, or part or all of the remaining reaction product can be directly subjected to hydrogenation.

If part of the alkylaryl hydroperoxide is converted into phenol and ketone and/or aldehyde, it is preferred that the alkylaryl is cumene as this gives phenol and acetone in step (iii).

In step (ii), alkylaryl hydroperoxide obtained in step (i) is contacted with olefin in the presence of a catalyst to obtain an oxirane compound and hydroxyalkylaryl. A catalyst which can suitably used in such process comprises titanium on silica and/or silicate. A preferred catalyst is described in EP-B-345856, the disclosure of which is herein incorporated by reference. The reaction generally proceeds at moderate temperatures and pressures, in particular at temperatures in the range of from 0 to 200° C., preferably in the range from 25 to 200° C. The precise pressure is not critical as long as it suffices to maintain the reaction mixture in a liquid condition. Atmospheric pressure may be satisfactory. In general, pressures can be in the range of from about 1 to about $100 \times 10^5$ N/m$^2$.

The olefin to be used in the process in the present invention depends on the oxirane compound to be prepared. Preferably, the olefin contains from 2 to 10 carbon atoms, more preferably from 2 to 8 carbon atoms. Most preferably, the olefin is propene.

At the conclusion of the epoxidation reaction, the liquid mixture comprising the desired products is separated from the catalyst. The oxirane compound can then be separated from the reaction product in any way known to be suitable to someone skilled in the art. The liquid reaction product may be worked up by fractional distillation, selective extraction and/or filtration. The catalyst, any solvent which might be present and any unreacted olefin or alkylaryl hydroperoxide may be recycled for further utilization.

Process step (ii) can be carried out with the catalyst in the form of a slurry, of a moving bed or a fluidized bed. However, a fixed bed is preferred for large-scale industrial application. The process may be carried out in a batch-wise manner, semi-continuously or continuously. The liquid containing the reactants may then be passed through the catalyst bed, so that the effluent from the reaction zone is substantially free from catalyst.

Subsequently, at least part of the reaction product stream containing hydroxyalkylaryl from which an oxirane compound has been separated off, is subjected to hydrogenation. A hydrogenation treatment which can be used comprises contacting reaction product with hydrogen at a temperature of from about 140 to about 330° C., preferably of from about 180 to about 320° C., and a pressure of from about 0.1 to about $10 \times 10^5$ N/m$^2$. The hydrogenation treatment is preferably carried out in the presence of a hydrogenation catalyst. Generally, the hydrogenation catalyst will contain a metal on a solid carrier which metal catalyses hydrogenation. Preferred catalysts are catalysts containing from 0.5 to 5% wt of metal or a metal compound on a carrier. Preferably, the metal present as metal or metal compound is one or more metal chosen from Group 1b, 2b, 3a, 4a, 4b, 5b, 6b, 7b and 8 of the Periodic Table of the Elements described in the Handbook of Chemistry and Physics, 63rd Edition. Catalysts which have been found to be suitable are the catalysts described in U.S. Pat. No. 5,475,159, the description of which is herein incorporated by reference. Further preferred catalyst are described in PCT/EP99/04275, the description of which is herein incorporated by reference.

After hydrogenation, the hydrogenated product can be recycled in total or in part. If only part of the hydrogenated product is recycled, the desired fraction can be separated off in any way suitable to someone skilled in the art.

The process according to the present invention is illustrated by the following Examples.

EXAMPLE 1

The epoxidation catalyst was a catalyst containing titanium on silica which was prepared as described in the Example according to the teaching of EP-A-345856, the description of which is herein incorporated by reference.

The hydrogenation catalyst was a catalyst containing copper, zinc and zirconium prepared according to Example 3 of U.S. Pat. No. 5,475,159, incorporated herein by reference.

Fresh cumene and recycled cumene were fed to a reactor. During 8 hours, air was bubbled in at the bottom of the reactor and left at the top of the reactor. The reactor was cooled during the reaction due to the exothermic nature of the oxidation. The reaction product obtained contained 28% wt of cumene hydroperoxide, 70% wt of cumene and 2% wt of further compounds.

A reaction mixture containing about 6 mole of 1-octene per mole of cumene hydroperoxide was fed to a reactor containing the fresh epoxidation catalyst described above at a temperature of 40° C. Octene oxide was separated off. It was found that 55% wt of 1-octene was converted into octene oxide.

A mixture containing 17% wt of 2-phenyl-2-propanol and 83% wt of cumene was contacted with hydrogen in the presence of the hydrogenation catalyst described above at a temperature of 140° C. and a pressure of $20 \times 10^5$ N/m$^2$ during 2 hours. The product obtained contained 10% wt of 2-phenyl-2-propanol, 86% wt of cumene, and 4% wt of alpha methyl styrene.

EXAMPLE 2

A mixture containing 17% wt of 2-phenyl-2-propanol and 83% wt of cumene was contacted with hydrogen in the presence of a hydrogenation catalyst comprising 5% wt of palladium on a charcoal carrier, at a temperature of 225° C. and a pressure of $20 \times 10^5$ N/m$^2$ during 2 hours. The product obtained contained 1% wt of 2-phenyl-2-propanol, 94% wt of cumene, 3% wt of i-propylcyclohexane and 2% wt of further compounds.

EXAMPLE 3

The experiment of Example 2 was repeated with the difference that the temperature was 280° C. The product obtained contained no 2-phenyl-2-propanol, 89% wt of cumene, 10% wt of i-propylcyclohexane and 1% wt of further compounds.

EXAMPLE 4

Fresh ethylbenzene and recycled ethylbenzene were fed to a reactor. During 8 hours, air was bubbled in at the bottom of the reactor and left at the top of the reactor. The reactor was cooled during the reaction due to the exothermic nature of the oxidation. The reaction product obtained contained 10% wt of ethyl benzene hydroperoxide, 88% wt of ethylbenzene and 2% wt of further compounds.

A reaction mixture containing about 6 mole of 1-octene per mole of ethylbenzene hydroperoxide was fed to a reactor containing the fresh epoxidation catalyst described in Example 1 at a-temperature of 40° C. Octene oxide was separated off. It was found that 41% wt of 1-octene was converted into octene oxide.

What is claimed is:

1. A process for preparing oxirane compounds, which process comprises the steps of:

(i) oxidizing an alkylaryl to obtain a stream comprising alkylaryl hydroperoxide, (ii) contacting at least part of the alkylaryl hydroperoxide obtained in step (i) with an olefin in the presence of a catalyst comprising titanium in combination with silica and/or silicate to obtain a product stream comprising an oxirane compound and alkylaryl hydroxyl, (iii) reacting part of the alkylaryl hydroperoxide obtained in step (i) to obtain a mixture comprising (a) phenol, and (b) a ketone and/or aldehyde, and (c) optionally by-products, (iv) separating oxirane compound from the product stream of step (ii) to obtain (a) a residual product stream and (b) oxirane, and (v) contacting at least a part of the residual product stream with hydrogen in the presence of a catalyst comprising a copper compound, a zinc compound and at least one compound selected from the group consisting of aluminum, zirconium, magnesium, a rare earth metal and mixtures thereof to obtain alkylaryl, wherein at least a part of said alkylaryl is recycled to step (i).

2. The process according to claim 1, in which process the alkylaryl compound is an alkylbenzene in which the alkyl substituent is a branched alkyl substituent comprising from 3 to 10 carbon atoms.

3. The process according to claim 1, in which process the alkylaryl compound is selected from the group comprising (i) cumene, (ii) di(iso-propyl)benzene, and (iii) a mixture of cumene and di(iso-propyl)benzene.

4. The process according to claim 1, in which at least a part of the by-products (c)obtained in step (iii) are sent to step (v).

5. The process according to claim 1, in which in step (ii) alkylaryl hydroperoxide is contacted with olefin at a temperature in the range of from about 0 to about 200° C., and a pressure in the range of from about 1 to about $100 \times 10^5$ $N/m^2$.

6. The process according to claim 1 , in which the hydrogenation of in process step (v) is carried out a temperature of from about 140 to about 330° C., and a pressure of from about 0.1 to about $50 \times 10^5$ $N/m^2$ in the presence of a hydrogenation catalyst.

7. The process as claimed in claim 1, wherein at least a part of the phenol and ketone and/or aldehyde are separated from said mixture of step (iii), and at least a part of the remaining mixture is sent to step (v).

8. The process as claimed in claim 1, wherein said catalyst comprises copper, zinc, and zirconium.

9. The process as claimed in claim 1, wherein said catalyst comprises from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.05 percent by weight to about 30 percent by weight, basis the total weight of the catalyst, of zirconium.

10. A process for preparing propylene oxide, which process comprises the steps of:

(i) oxidizing cumene to obtain a stream comprising cumene hydroperoxide, (ii) contacting at least part of the cumene hydroperoxide obtained in step (i) with propylene in the presence of a catalyst comprising titanium in combination with silica and/or silicate to obtain a product stream comprising propylene oxide and cumyl alcohol, (iii) reacting part of the cumene hydroperoxide obtained in step (i) to obtain a mixture comprising (a) phenol, and (b) a ketone and/or aldehyde, and (c) optionally by-products, (iv) separating oxirane compound from the product stream of step (ii) to obtain (a) a residual product stream and (b) propylene oxide, and (v) contacting at least a part of the residual product stream with hydrogen in the presence of a catalyst comprising a copper compound, a zinc compound and at least one compound selected from the group consisting of aluminum, zirconium, magnesium, a rare earth metal and mixtures thereof to obtain cumene, wherein at least a part of said cumene is recycled to step (i).

11. A process for preparing oxirane compounds, which process comprises the steps of:

(i) oxidizing an alkylaryl to obtain a stream comprising alkylaryl hydroperoxide, (ii) contacting at least part of the alkylaryl hydroperoxide obtained in step (i) with an olefin in the presence of a catalyst comprising titanium in combination with silica and/or silicate to obtain a product stream comprising an oxirane compound and alkylaryl hydroxyl, (iii) separating oxirane compound from the product stream of step (ii) to obtain (a) a residual product stream and (b) oxirane, and (iv) contacting at least a part of the residual product stream with hydrogen in the presence of a catalyst comprising (a) from about 10 percent by weight to about 80 percent by weight, calculated as the oxide, basis the total weight of the catalyst, of copper, (b) zinc, and (c) at least one compound selected from the group consisting of aluminum, zirconium, magnesium, a rare earth and mixtures thereof, to obtain alkylaryl, wherein at least a part of said alkylaryl is recycled to step (i).

12. The process as claimed in claim 11, wherein said oxirane is propylene oxide, and said olefin is propylene.

13. The process as claimed in claim 12, wherein said alkylaryl is cumene.

14. The process as claimed in claim 12, wherein said alkylaryl is di(isopropyl)benzene.

15. A process for preparing propylene oxide, which process comprises the steps of:

(i) oxidizing cumene to obtain a stream comprising cumene hydroperoxide, (ii) contacting at least part of the cumene hydroperoxide obtained in step (i) with propylene in the presence of a catalyst comprising titanium in combination with silica and/or silicate to obtain a product stream comprising propylene oxide and cumyl alcohol, (iii) separating oxirane compound from the product stream of step (ii) to obtain (a) a residual product stream and (b) propylene oxide, and (iv) contacting at least a part of the residual product stream with hydrogen in the presence of a catalyst comprising (a) from about 10 percent by weight to about 80 percent by weight, calculated as the oxide, basis the total weight of the catalyst, of copper, (b) zinc, and (c) at least one compound selected from the group consisting of aluminum, zirconium, magnesium, a rare earth and mixtures thereof, wherein at least a part of said cumene is recycled to step (i).

16. The process as claimed in claim 15, wherein said catalyst comprises from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.05 percent by weight to about 30 percent by weight, basis the total weight of the catalyst, of zirconium.

* * * * *